(12) United States Patent
Fantuzzi

(10) Patent No.: US 8,617,541 B2
(45) Date of Patent: *Dec. 31, 2013

(54) SOLUBILIZED COQ-10

(75) Inventor: Michael Fantuzzi, Glendale, CA (US)

(73) Assignee: Soft Gel Technologies, Inc., Los Angeles, CA (US)

( * ) Notice: Subject to any disclaimer, the term of this patent is extended or adjusted under 35 U.S.C. 154(b) by 19 days.

This patent is subject to a terminal disclaimer.

(21) Appl. No.: 13/365,244

(22) Filed: Feb. 2, 2012

(65) Prior Publication Data

US 2012/0128769 A1    May 24, 2012

Related U.S. Application Data

(63) Continuation of application No. 10/674,268, filed on Sep. 29, 2003, now Pat. No. 8,124,072.

(51) Int. Cl.
*A61K 31/122* (2006.01)
*A61K 31/05* (2006.01)
*A61K 9/48* (2006.01)

(52) U.S. Cl.
USPC .......... 424/94.1; 514/688; 514/731; 424/455; 424/456

(58) Field of Classification Search
USPC ........... 424/94.1; 514/688, 731; 434/455, 456
See application file for complete search history.

(56) References Cited

U.S. PATENT DOCUMENTS

| | | |
|---|---|---|
| 4,029,760 A | 6/1977 | De Roeck |
| 4,343,816 A | 8/1982 | Cavazza |
| 4,559,222 A | 12/1985 | Enscore et al. |
| 4,565,700 A | 1/1986 | Suzuki |
| 4,599,232 A | 7/1986 | Bertelli |
| 4,687,782 A | 8/1987 | Brantman |
| 4,824,669 A | 4/1989 | Folkers et al. |
| 4,840,970 A | 6/1989 | Ohasi et al. |
| 5,030,458 A | 7/1991 | Shug et al. |
| 5,240,961 A | 8/1993 | Shug |
| 5,290,605 A | 3/1994 | Shapira |
| 5,298,246 A | 3/1994 | Yano et al. |
| 5,310,578 A | 5/1994 | Thurn-Muller et al. |
| 5,362,753 A | 11/1994 | Blum et al. |
| 5,378,461 A | 1/1995 | Neigut |
| 5,391,550 A | 2/1995 | Carniglia et al. |
| 5,431,916 A | 7/1995 | White |
| 5,500,416 A | 3/1996 | Miyazawa et al. |
| 5,504,072 A | 4/1996 | Schmidl et al. |
| 5,512,691 A | 4/1996 | Barnicki et al. |
| 5,532,002 A | 7/1996 | Story |
| 5,552,167 A | 9/1996 | Taylor et al. |
| 5,560,928 A | 10/1996 | Defelice |
| 5,591,772 A | 1/1997 | Lane et al. |
| 5,626,849 A | 5/1997 | Hastings et al. |
| 5,637,316 A | 6/1997 | Ribier et al. |
| 5,645,856 A | 7/1997 | Lacy et al. |
| 5,670,320 A | 9/1997 | Wallace et al. |
| 5,686,491 A | 11/1997 | Sherwood |
| 5,716,928 A | 2/1998 | Benet et al. |
| 5,756,291 A | 5/1998 | Griffin et al. |
| 5,843,476 A | 12/1998 | Ribier et al. |
| 5,858,401 A | 1/1999 | Bhalani et al. |
| 5,889,062 A | 3/1999 | Hoppe et al. |
| 5,891,469 A | 4/1999 | Amselem |
| 5,912,272 A | 6/1999 | Hoppe et al. |
| 5,916,591 A | 6/1999 | Bierdel-Willkommen et al. |
| 5,948,443 A | 9/1999 | Riley et al. |
| 5,968,987 A | 10/1999 | Charman et al. |
| 5,976,568 A | 11/1999 | Riley |
| 5,977,162 A | 11/1999 | Seidman |
| 5,980,939 A | 11/1999 | Kim et al. |
| 5,985,344 A | 11/1999 | Cherukuri et al. |
| 6,008,192 A | 12/1999 | Al-Razzak et al. |
| 6,020,383 A | 2/2000 | Stone et al. |
| 6,033,678 A | 3/2000 | Lorenzen |
| 6,048,846 A | 4/2000 | Cochran |
| 6,048,886 A | 4/2000 | Neigut |
| 6,054,136 A | 4/2000 | Farah et al. |
| 6,056,971 A | 5/2000 | Goldman |
| 6,063,432 A | 5/2000 | Maxwell et al. |
| 6,069,167 A | 5/2000 | Sokol |
| 6,080,788 A | 6/2000 | Sole et al. |
| 6,096,338 A | 8/2000 | Lacy et al. |
| 6,121,234 A | 9/2000 | Benet et al. |
| 6,174,547 B1 | 1/2001 | Dong et al. |
| 6,184,255 B1 | 2/2001 | Mae et al. |

(Continued)

FOREIGN PATENT DOCUMENTS

| | | |
|---|---|---|
| DE | 3512054 | 10/1986 |
| EP | 0 882 450 | 1/1998 |

(Continued)

OTHER PUBLICATIONS

Palamakula, et al., "Preparation and In Vitro Characterization of Self-Nanoemulsified Drug Delivery Systems of Coenzyme Q10 Using Chiral Essential Oil Components," Pharmaceutical Technology, Oct. 2004, pp. 74-88.

Office Action dated Aug. 21, 2012, U.S. Appl. No. 13/406,794, 8 pages.

Amendment and Response to Office Action dated Nov. 21, 2012, U.S. Appl. No. 13/406,794, 9 pages.

Final Office Action dated Dec. 14, 2012, U.S. Appl. No. 13/406,794, 7 pages.

Inter Partes Reexamination Proceeding for U.S. Patent 8,124,072, brought by Jarrow Formulas, Inc., Sep. 15, 2012, 525 pages.

Inter Partes Reexamination Proceeding for U.S. Patent 8,105,583, brought by Jarrow Formulas, Inc., Sep. 15, 2012, 557 pages.

Inter Partes Reexamination Proceeding for U.S. Patent 8,147,826, brought by Jarrow Formulas, Inc., Sep. 15, 2012, 556 pages.

Order Construing Claims and Granting Defendants' Motion for Summary Judgment entered Aug. 2, 2012, CV 10-0301 PSG (JCx), *Jarrow Formulas, Inc.* v. *Now Health Group, Inc.*, 28 pages.

(Continued)

*Primary Examiner* — Rosanne Kosson
(74) *Attorney, Agent, or Firm* — Dorsey & Whitney LLP

(57) ABSTRACT

The present invention is directed to compositions and methods of delivery of CoQ-10 solubilized in monoterpenes. Use of monoterpenes as dissolving agents, greatly effects the ability to incorporate greater amounts of bioactive CoQ-10 in formulations, such as soft gel capsules.

40 Claims, No Drawings

(56) References Cited

U.S. PATENT DOCUMENTS

| | | | |
|---|---|---|---|
| 6,197,349 | B1 | 3/2001 | Westesen et al. |
| 6,200,550 | B1 | 3/2001 | Masterson et al. |
| 6,203,818 | B1 | 3/2001 | Vester |
| 6,207,137 | B1 | 3/2001 | Shuch et al. |
| 6,218,436 | B1 | 4/2001 | Howard et al. |
| 6,232,346 | B1 | 5/2001 | Sole et al. |
| 6,261,575 | B1 | 7/2001 | Hoppe et al. |
| 6,267,985 | B1 | 7/2001 | Chen et al. |
| 6,277,431 | B1 | 8/2001 | Berry et al. |
| 6,284,268 | B1 | 9/2001 | Mishra et al. |
| 6,300,361 | B1 | 10/2001 | Vivilecchia et al. |
| 6,300,377 | B1 | 10/2001 | Chopra |
| 6,335,361 | B1 | 1/2002 | Hamilton |
| 6,342,526 | B1 | 1/2002 | Vervuert et al. |
| 6,365,181 | B1 | 4/2002 | Matthews |
| 6,368,618 | B1 | 4/2002 | Jun et al. |
| 6,426,362 | B1 | 7/2002 | Miller et al. |
| 6,428,779 | B1 | 8/2002 | Sauermann et al. |
| 6,436,431 | B1 | 8/2002 | Hoffpauer et al. |
| 6,441,050 | B1 | 8/2002 | Chopra |
| 6,455,589 | B1 | 9/2002 | Ames et al. |
| 6,469,024 | B2 | 10/2002 | Tino et al. |
| 6,472,378 | B2 | 10/2002 | von Borstel |
| 6,479,069 | B1 | 11/2002 | Hamilton |
| 6,503,483 | B2 | 1/2003 | Shuch et al. |
| 6,503,506 | B1 | 1/2003 | Germano |
| 6,503,523 | B2 | 1/2003 | Hoppe et al. |
| 6,506,915 | B1 | 1/2003 | West |
| 6,528,042 | B1 | 3/2003 | Brown et al. |
| 6,545,184 | B1 | 4/2003 | Lipshutz |
| 6,552,004 | B1 | 4/2003 | Elazhary et al. |
| 6,562,869 | B1 | 5/2003 | Hamilton et al. |
| 6,569,463 | B2 | 5/2003 | Patel et al. |
| 6,579,854 | B1 | 6/2003 | Mitchell et al. |
| 6,616,942 | B1 | 9/2003 | Udel |
| 6,623,734 | B2 | 9/2003 | Udell et al. |
| 6,630,170 | B2 | 10/2003 | Balkus et al. |
| 6,664,287 | B2 | 12/2003 | Avery et al. |
| 6,730,319 | B2 | 5/2004 | Maeder et al. |
| 6,740,338 | B1 | 5/2004 | Chopra |
| 6,782,307 | B2 | 8/2004 | Wilmott et al. |
| 6,790,465 | B2 | 9/2004 | Weissman |
| 6,806,259 | B2 | 10/2004 | Udell et al. |
| 6,855,733 | B2 | 2/2005 | Udell et al. |
| 6,955,820 | B1 | 10/2005 | Udell |
| 7,015,245 | B2 | 3/2006 | Rich et al. |
| 7,026,361 | B2 | 4/2006 | Minemura et al. |
| 7,060,263 | B2 | 6/2006 | Udell et al. |
| 7,169,385 | B2 | 1/2007 | Fantuzzi et al. |
| 7,182,950 | B2 | 2/2007 | Garti et al. |
| 7,220,429 | B2 | 5/2007 | Udell |
| 7,273,606 | B2 | 9/2007 | Fantuzzi et al. |
| 7,273,622 | B2 | 9/2007 | Udell et al. |
| 7,588,786 | B2 | 9/2009 | Khan et al. |
| 7,713,523 | B2 | 5/2010 | Fantuzzi et al. |
| 7,815,943 | B2 | 10/2010 | Hennen |
| 8,097,279 | B2 | 1/2012 | Hassan et al. |
| 8,105,583 | B2 * | 1/2012 | Fantuzzi ............ 424/94.1 |
| 8,124,072 | B2 * | 2/2012 | Fantuzzi ............ 424/94.1 |
| 8,147,826 | B2 | 4/2012 | Fantuzzi |
| 2002/0098172 | A1 | 7/2002 | Udell et al. |
| 2003/0082168 | A1 | 5/2003 | Yegorova |
| 2003/0108600 | A1 | 6/2003 | Okibayashi et al. |
| 2003/0147921 | A1 | 8/2003 | Khan et al. |
| 2003/0176500 | A1 | 9/2003 | Molly et al. |
| 2003/0232076 | A1 | 12/2003 | Makino et al. |
| 2003/0232095 | A1 * | 12/2003 | Garti et al. ............ 424/725 |
| 2004/0001874 | A1 | 1/2004 | Davidson et al. |
| 2004/0047922 | A1 | 3/2004 | Elstner |
| 2004/0166157 | A1 | 8/2004 | Thombre |
| 2005/0025756 | A1 | 2/2005 | Erwin |
| 2005/0031681 | A1 | 2/2005 | Udell et al. |
| 2005/0036998 | A1 | 2/2005 | Udell |
| 2005/0037066 | A1 | 2/2005 | Udell et al. |
| 2007/0269508 | A1 | 11/2007 | Udel |
| 2008/0003279 | A1 | 1/2008 | Udell |
| 2008/0020022 | A1 | 1/2008 | Udell |
| 2008/0089877 | A1 | 4/2008 | Udell et al. |
| 2008/0226710 | A1 | 9/2008 | Fantuzzi |
| 2012/0121566 | A1 | 5/2012 | Fantuzzi |
| 2012/0153519 | A1 | 6/2012 | Fantuzzi |
| 2013/0129821 | A1 | 5/2013 | Fantuzzi |

FOREIGN PATENT DOCUMENTS

| | | |
|---|---|---|
| EP | 0 888 774 | 1/1999 |
| EP | 888774 A2 * | 1/1999 |
| EP | 1 728 506 | 3/2006 |
| JP | 55081813 | 6/1980 |
| JP | 5770815 | 5/1982 |
| JP | S57142911 | 9/1982 |
| JP | 59172417 | 9/1984 |
| WO | WO 88/03015 | 5/1988 |
| WO | WO 98/40086 | 9/1998 |
| WO | WO 98/56368 | 12/1998 |
| WO | WO 00/51574 | 9/2000 |
| WO | WO 01/52822 | 7/2001 |
| WO | WO 02/09685 | 2/2002 |
| WO | WO 03/105607 | 12/2003 |
| WO | WO 2004/066925 | 8/2004 |
| WO | WO 2005/032278 | 4/2005 |
| WO | WO 2005/092123 | 10/2005 |

OTHER PUBLICATIONS

Amendment filed Jan. 15, 2008, to Office Action dated Sep. 17, 2007, U.S. Appl. No. 10/293,932, 16 pages.

Amendment filed Mar. 11, 2009, to Office Action dated Sep. 11, 2008, U.S. Appl. No. 10/293,932, 16 pages.

Third Party Requestor's Comments under 35 C.F.R. 314(B)(2) and 37 C.F.R. 1.947 in Inter Partes Reexamination of U.S. Patent 8,124,072, Feb. 22, 2013, 74 pages.

Third Party Requestor's Comments under 35 C.F.R. 314(B)(2) and 37 C.F.R. 1.947 in Inter Partes Reexamination of U.S. Patent 8,105,583, Feb. 22, 2013, 52 pages.

Third Party Requestor's Comments under 35 C.F.R. 314(B)(2) and 37 C.F.R. 1.947 in Inter Partes Reexamination of U.S. Patent 8,147,826, Feb. 22, 2013, 33 pages.

Amendment and Response to Final Office Action dated Mar. 14, 2013, U.S. Appl. No. 13/406,794, 8 pages.

Advisory Action dated Mar. 28, 2013, U.S. Appl. No. 13/406,794, 3 pages.

Anderson U.S. Appl. No. 60/253,874, David M. Anderson, Applicant, filed Nov. 29, 2000, 21 pages.

Al-Hasso, Shahla, "Coenzyme Q10: A Review," *Hospital Pharmacy*, vol. 36, No. 1, pp. 51-55, 2000 Facts and Comparisons.

Author Unknown, "pformulate: A Soft Gell!!" 2000, pp. 1-6, found at URL: http://www.pformulate.com/pformsoftgel.htm.

Author Unknown, Paul Karrer Biography, Nobel Prizes, Nobel Prize in Chemistry, nobelprize.org, printed on Jan. 5, 2007, 2 pages.

Author Unknown, Oilseeds International Ltd., Rice bran oil—a health benefit, http://www.oilseedssf.com/products/prod.rice.html, 2002, printed on Mar. 6, 2006; 2 pages.

Bhandari, et al., "Preparation, Characterization and Evaluation of Coenzyme Q10 Binary Solid Dispersions for Enhanced Solubility and Dissolution," *Biol Pharm. Bull.*, 2007, vol. 30, No. 6, pp. 1171-1176.

Bliznakov, et al., "Biochemical and Clinical Consequencs of Inhibiting Coenzyme Q10 Biosynthesis by Lipid-Lowering HMG-CoA Reductase Inhibitors (Statins): A Critical Overview," *Advances in Therapy*, Jul./Aug. 1998, vol. 15, No. 4, pp. 218-228.

Chopra, et al., "Relative Bioavailability of Coenzyme Q10 Formulations in Human Subjects," *Internat. J. Vit. Nutr. Res.*, 1998, vol. 68, pp. 109-113.

Chopra, et al., "A New Coenzyme Q10 Preparation with Enhanced Bioavailability," *FASEB Journal*, 1997, vol. 11, No. 3, pp. A586 (Abstract).

Comax Q10 Trademark Registration Abstract and Specimen, Registration No. 1764014, registered Apr. 13, 1993, 26 pages.

(56) References Cited

OTHER PUBLICATIONS

Constantinescu, et al., "A Randomized Study of the Bioavailability of Different Formulations of Coenzyme Q10 (Ubiquinon)," The Journal of Clinical Pharmacology, 2007; 47: 1580-1586.
CRC Handbook of Chemistry and Physics, 51st Edition, R.C. Weast (Editor), The Chemical Rubber Co., Cleveland, Ohio, 1970, pp. C-309, 356, 364, 392, 434 and 488.
Density of Cooking Oil, *The Physics Factbook*, edited by Glenn Elert, dated unknown, 3 pages.
Dictionary.com accessed on Jan. 17, 2007, "thixotropic" 1 page.
Grant & Hackh's Chemical Dictionary, Definition of Gelatin, Fifth Edition, McGraw-Hill Book Company, 1987, p. 258.
Greenberg, et al., "Co-enzyme Q10: a new drug for cardiovascular disease," *The Journal of Clinical Pharmacology*, 1990, vol. 30, pp. 596-608.
Kang et al., "Physicochemical studies of lidocaine-menthol binary systems for enhanced membrane transport," *International Journal of Pharmaceutics*, 206 (2000) 35-42.
Kaplun-Frischoff, et al., "Testosterone Skin Permeation Enhancement by Menthol through Formation of Eutectic with Drug and Interaction with Skin Lipids," Journal of Pharmaceutical Sciences, vol. 86, No. 12, Dec. 1997, pp. 1394-1399.
Kommuru, et al., "A simplified chromatographic method for quantitative determination of coenzyme Q10 in dog plasma," *Journal of Pharmaceutical and Biomedical Analysis*, 16 (1998) 1037-1040.
Kommuru, et al., "Racemate and Enantiomers of Ketoprofen: Phase Diagram, Thermodynamic Studies, Skin Permeability, and Use of Chiral Permeation Enhancers," *Journal of Pharmaceutical Sciences* vol. 87, No. 7, Jul. 1998, pp. 833-840.
Kommuru, et al., "Self-emulsifying drug delivery systems (SEDDS) of coenzyme Q10: formulation development and bioavailabiilty assessment," *International Journal of Pharmaceutics*, 2001, vol. 212, pp. 233-246.
Kommuru, et al., "Stability and Bioequivalence Studies of Two Marketed Formulations of Coenzyme Q10 in Beagle Dogs," *Chem. Pharm. Bull.* 47(7) 1024-1028 (1999).
Merriam-Webster Dictionary OnLine, definition of "elixir," http://www.merriam-webster.com/dictionary/elixir, printed from the Jun. 3, 2009, 2 pages.
Nazzal et al., "Preparation and in vitro characterization of a eutectic based semisolid self-nanoemulsified drug delivery system (SNEDDS) of ubiquinone: mechanism and progress of emulsion formation," *International Journal of Pharmaceutics* 235 (2002) 247-265.
Nazzal et al., "Response Surface Methodology for the Optimization of Ubiquinone Self-Nonoemulsified Drug Delivery System," *AAPSPharmSciTech 2002*; 3 (1) article 3, pp. 1-9, Published: Feb. 8, 2002, found at URL: http://www.aapspharmscitech.org.
Padilla-Zakour, "Chemical Food Preservatives: Bonzoate and sorbate," *Venture*, New York State Agriculture Experimental Station, 1998, vol. 1, No. 2, 3 pages, found at URL: http://www.nysaes.cornell.edu/necfe/pubs/pdf/Venture/venture2_chemical.html.
Pouton, Colin W., "Lipid formulations for oral administration of drugs: non-emulsifying, self-emulsifying and 'self-microemulsifying' drug delivery systems," *European Journal of Pharmaceutical Sciences* 11 Suppl. 2 (2000) S93-S98.
RITO Partnership, Rice Bran Oil Info, http://web.archive.org/web/20020809203831/http://www.ricebranoil.info/why/index.html, web page of Aug. 9, 2002, printed from the Internet on Apr. 29, 2009, 1 page.
Shojaei et al., "Transbuccal permeation of a nucleoside analog, dideoxycytidine: effects of menthol as a permeation enhancer," *International Journal of Pharmaceutics* 192 (1999) 139-146.
Shrestha et al., "Aqueous Phase Behavior of Diglycerol Fatty Acid Esters," *Journal of Dispersion Science and Technology*, 28: pp. 883-891, 2007.
Siekmann et al., "Preparation and Physicochemical Characterization of Aqueous Dispersions of Coenzyme Q10 Nanoparticles," *Pharmaceutical Research*, vol. 12, No. 2, 1995.
Walker, "Mass, Weight, Density or Specific Gravity of Liquids, Specific Gravity of Liquids," 2007, Slmetric.co.uk [http://www.simetric.co.uk/si_liquids.htm], 5 pages.
Weber, et al., "Intestinal Absorption of Coenzyme Q10 Administered in a Meal or as Capsules to Healthy Subjects," *Nutrition Research*, vol. 17, No. 6, pp. 941-945, 1997.
Weis, et al., "Bioavailability of Four Oral Coenzyme Q10 Formulations in Health Volunteers," *Molec. Aspects. Med.*, 1994, vol. 15, Supplement, pp. s273-s280.
Office Action (Restriction Requirement) dated Jan. 7, 2005, U.S. Appl. No. 10/674,268, 9 pages.
Response to Restriction Requirement dated Feb. 7, 2005, U.S. Appl. No. 10/674,268, 2 pages.
Office Action dated Mar. 11, 2005, U.S. Appl. No. 10/674,268, 8 pages.
Amendment and Response under 37 C.F.R. 1.111 dated Jun. 7, 2005, U.S. Appl. No. 10/674,268, 10 pages.
Office Action (Restriction Requirement) dated Jun. 28, 2005, U.S. Appl. No. 10/674,268, 7 pages.
Response to Restriction Requirement dated Jul. 27, 2005, U.S. Appl. No. 10/674,268, 10 pages.
Notice of Allowance and Fee(s) Due dated Aug. 26, 2005, U.S. Appl. No. 10/674,268, 11 pages.
Request for Continued Examination dated Sep. 15, 2005, U.S. Appl. No. 10/674,268, 1 page.
Declaration Under 37 C.F.R. 1.131 Antedating a Reference, dated Sep. 15, 2005, U.S. Appl. No. 10/674,268, 2 pages.
Office Action dated Sep. 30, 2005, U.S. Appl. No. 10/674,268, 8 pages.
Amendment and Response dated Dec. 20, 2005, U.S. Appl. No. 10/674,268, 13 pages.
Final Office Action dated Jan. 31, 2006, U.S. Appl. No. 10/674,268, 7 pages.
Response to Office Action Made Final, dated Apr. 28, 2006, U.S. Appl. No. 10/674,268, 14 pages.
Advisory Action dated May 22, 2006, U.S. Appl. No. 10/674,268, 4 pages.
Notice of Appeal dated May 31, 2006, U.S. Appl. No. 10/674,268, 2 pages.
Request for Continued Examination and Response to Office Action Made Final and Advisory Action dated Aug. 31, 2006, U.S. Appl. No. 10/674,268, 14 pages.
Final Office Action dated Sep. 15, 2006, U.S. Appl. No. 10/674,268, 8 pages.
Notice of Appeal dated Mar. 15, 2007, U.S. Appl. No. 10/674,268, 2 pages.
Request for Continued Examination and Response to Office Action Made Final dated Jul. 12, 2007, 16 pages.
Final Office Action dated Aug. 2, 2007, U.S. Appl. No. 10/674,268, 9 pages.
Response to Office Action Made Final, dated Oct. 8, 2007, U.S. Appl. No. 10/674,268, 11 pages.
Declaration Under Rule 1.131, dated Oct. 8, 2007, U.S. Appl. No. 10/674,268, 30 pages.
Advisory Action dated Oct. 25, 2007, U.S. Appl. No. 10/674,268, 14 pages.
Request for Continued Examination dated Oct. 30, 2007, U.S. Appl. No. 10/674,268, 2 pages.
Declaration Under Rule 1.131 dated Feb. 12, 2008, U.S. Appl. No. 10/674,268, 2 pages.
Interview Summary dated Mar. 3, 2008, U.S. Appl. No. 10/674,268, 3 pages.
Final Office Action dated Apr. 10, 2008, U.S. Appl. No. 10/674,268 6 pages.
Amendment and Response to Final Office Action dated Sep. 22, 2008, 17 pages.
Advisory Action dated Sep. 30, 2008, U.S. Appl. No. 10/674,268, 7 pages.
Notice of Appeal dated Oct. 10, 2008, U.S. Appl. No. 10/674,268, 2 pages.
Request for Continued Examination and Amendment and Response to Advisory Action of Sep. 30, 2008 and to Office Action of Apr. 10, 2008, dated Apr. 10, 2009, U.S. Appl. No. 10/674,268, 11 pages.

(56) References Cited

OTHER PUBLICATIONS

Office Action dated May 19, 2009, U.S. Appl. No. 10/674,268, 11 pages.
Amendment and Response to Office Action dated Oct. 19, 2009, U.S. Appl. No. 10/674,268, 11 pages.
Final Office Action dated Nov. 18, 2009, U.S. Appl. No. 10/674,268, 11 pages.
Examiner's Interview Summary dated Feb. 23, 2010, U.S. Appl. No. 10/674,268, 4 pages.
Notice of Appeal and Interview Summary dated May 18, 2010, U.S. Appl. No. 10/674,268, 2 page.
Examiner's Interview Summary dated May 20, 2010, U.S. Appl. No. 10/674,268, 4 pages.
Request for Continued Examination, Amendment and Response to Final Office Action, U.S. Appl. No. 10/674,268, dated Dec. 17, 2010, 12 pages.
Office Action dated Jan. 12, 2011, U.S. Appl. No. 10/674,268, 14 pages.
Amendment and Response to Office Action dated Jun. 13, 2011, U.S. Appl. No. 10/674,268, 13 pages.
Office Action dated Jul. 6, 2011, U.S. Appl. No. 10/674,268, 12 pages.
Notice of Allowance and Fee(s) Due dated Oct. 19, 2011, U.S. Appl. No. 10/674,268, 7 pages.
Office Action (Restriction Requirement) dated Jun. 17, 2005, U.S. Appl. No. 10/792,648, 10 pages.
Response to Restriction Requirement dated Jun. 29, 2005, U.S. Appl. No. 10/792,648, 8 pages.
Notice of Allowance and Fee(s) Due and Interview Summary dated Jul. 29, 2005, U.S. Appl. No. 10/792,648, 12 pages.
Request for Continued Examination dated Sep. 14, 2005, U.S. Appl. No. 10/792,648, 2 pages.
Notice of Allowance and Fee(s) Due dated Sep. 30, 2005, U.S. Appl. No. 10/792,648, 5 pages.
Request for Continued Examination dated Oct. 14, 2005, U.S. Appl. No. 10/792,648, 2 pages.
Notice of Allowance and Fee(s) Due dated Feb. 15, 2006, U.S. Appl. No. 10/792,648, 5 pages.
Restriction Requirement dated Oct. 31, 2005, U.S. Appl. No. 10/953,328, 5 pages.
Response to Restriction Requirement dated Nov. 29, 2005, U.S. Appl. No. 10/953,328, 8 pages.
Office Action dated Jan. 5, 2006, U.S. Appl. No. 10/953,328, 18 pages.
Amendment and Response dated Apr. 5, 2006, U.S. Appl. No. 10/953,328, 8 pages.
Office Action dated Apr. 26, 2006, U.S. Appl. No. 10/953,328, 9 pages.
Amendment and Response dated Oct. 26, 2006, U.S. Appl. No. 10/953,328, 14 pages.
Office Action (Restriction Requirement) dated Nov. 17, 2006, U.S. Appl. No. 10/953,328, 7 pages.
Response to Restriction Requirement dated Dec. 15, 2006, U.S. Appl. No. 10/953,328, 9 pages.
Final Office Action dated Jan. 18, 2007, U.S. Appl. No. 10/953,328, 13 pages.
Request for Continued Examination and Amendment and Response to Final Office Action dated Jul. 12, 2007, U.S. Appl. No. 10/953,328, 17 pages.
Final Office Action dated Aug. 7, 2007, U.S. Appl. No. 10/953,328, 11 pages.
Amendment and Response to Final Office Action dated Ocober 5, 2007, U.S. Appl. No. 10/953,328, 8 pages.
Declaration Under Rule 1.131 filed Oct. 5, 2007, U.S. Appl. No. 10/953,328, 38 pages.
Request for Continued Examination dated Oct. 29, 2007, U.S. Appl. No. 10/953,328, 2 pages.
Advisory Action dated Nov. 1, 2007, U.S. Appl. No. 10/953,328, 4 pages.
Office Action dated Dec. 13, 2007, U.S. Appl. No. 10/953,328, 8 pages.
Declaration Under Rule 1.131 dated Feb. 12, 2008, U.S. Appl. No. 10/953,328, 2 pages.
Interview Summary dated Feb. 26, 2008, U.S. Appl. No. 10/953,328, 2 pages.
Amendment and Response to Office Action dated Apr. 14, 2008, U.S. Appl. No. 10/953,328, 28 pages.
Final Office Action dated Jun. 3, 2008, U.S. Appl. No. 10/953,328, 8 pages.
Amendment After Final (Under 37 C.F.R. 1.116) dated Nov. 3, 2008, U.S. Appl. No. 10/953,328, 19 pages.
Request for Continued Examination dated Nov. 25, 2008, U.S. Appl. No. 10/953,328, 2 pages.
Advisory Action dated Dec. 3, 2008, U.S. Appl. No. 10/953,328, 7 pages.
Final Office Action dated Jan. 21, 2009, U.S. Appl. No. 10/953,328, 9 pages.
Request for Continued Examination and Amendment and Response to Final Office Action dated May 21, 2009, U.S. Appl. No. 10/953,328, 22 pages.
Supplementary Declaration Pursuant to 37 C.F.R. 1.131 filed May 27, 2009, U.S. Appl. No. 10/953,328, 27 pages.
Interview Summary dated Jun. 1, 2009, U.S. Appl. No. 10/953,328, 3 pages.
Office Action dated Jun. 22, 2009, U.S. Appl. No. 10/953,328, 9 pages.
Amendment and Response to Office Action dated Sep. 22, 2009, U.S. Appl. No. 10/953,328, 9 pages.
Final Office Action dated Oct. 23, 2009, U.S. Appl. No. 10/953,328, 9 pages.
Notice of Appeal dated Feb. 23, 2010, U.S. Appl. No. 10/953,328, 1 page.
Appeal Brief dated Apr. 23, 2010, U.S. Appl. No. 10/953,328, 49 pages.
Examiner's Answer dated May 24, 2010, U.S. Appl. No. 10/953,328, 8 pages.
Decision on Appeal dated May 11, 2011, U.S. Appl. No. 10/953,328, 9 pages.
Office Action dated May 18, 2011, U.S. Appl. No. 10/953,328, 9 pages.
Amendment and Response to Office Action and Terminal Disclaimer dated Aug. 18, 2011, U.S. Appl. No. 10/953,328, 9 pages.
Terminal Disclaimer dated Sep. 2, 2011, U.S. Appl. No. 10/953,328, 2 pages.
Notice of Allowance and Fee(s) Due dated Sep. 21, 2011, U.S. Appl. No. 10/953,328, 11 pages.
Office Action dated Oct. 23, 2006, U.S. Appl. No. 11/206,718, 12 pages.
Amendment and Response dated Apr. 23, 2007, U.S. Appl. No. 11/206,718, 5 pages.
Terminal Disclaimer dated Apr. 23, 2007, U.S. Appl. No. 11/206,718, 2 pages.
Notice of Allowance and Fee(s) Due dated May 16, 2007, 7 pages.
Office Action (Restriction Requirement) dated Dec. 7, 2005, U.S. Appl. No. 11/223,718, 5 pages.
Amendment and Response dated Jan. 6, 2006, U.S. Appl. No. 11/223,718, 5 pages.
Office Action dated Mar. 15, 2006, U.S. Appl. No. 11/223,718, 7 pages.
Amendment and Response dated Sep. 14, 2006, U.S. Appl. No. 11/223,718, 18 pages.
Final Office Action dated Oct. 2, 2006, U.S. Appl. No. 11/223,718, 8 pages.
Notice of Appeal dated Apr. 2, 2007, U.S. Appl. No. 11/223,718, 2 pages.
Request for Continued Examination and Response to Final Office Action dated Jun. 26, 2007, U.S. Appl. No. 11/223,718, 21 pages.
Final Office Action dated Jul. 20, 2007, U.S. Appl. No. 11/223,718, 10 pages.
Request for Continued Examination and Response to Final Office Action dated Oct. 2, 2007, U.S. Appl. No. 11/223,718, 10 pages.

(56) References Cited

OTHER PUBLICATIONS

Declaration Under Rule 1.131 filed Oct. 2, 2007, U.S. Appl. No. 11/223,718, 19 pages.
Office Action dated Oct. 30, 2007, U.S. Appl. No. 11/223,718, 9 pages.
Response to Office Action dated Nov. 30, 2007, U.S. Appl. No. 11/223,718, 19 pages.
Final Office Action dated Jan. 9, 2008, U.S. Appl. No. 11/223,718, 9 pages.
Declaration Under Rule 1.131 dated Feb. 12, 2008, U.S. Appl. No. 11/223,718, 2 pages.
Interview Summary dated Feb. 25, 2008, U.S. Appl. No. 11/223,718, 2 pages.
Amendment After Final Under 37 C.F.R. 1.116 dated Apr. 9, 2008, U.S. Appl. No. 11/223,718, 39 pages.
Advisory Action dated Apr. 23, 2008, U.S. Appl. No. 11/223,718, 5 pages.
Notice of Appeal dated Jun. 9, 2008, U.S. Appl. No. 11/223,718, 2 pages.
Request for Continued Examination and Amendment After Final Under 37 C.F.R. 1.114 dated Oct. 9, 2008, 24 pages.
Final Office Action dated Nov. 17, 2008, U.S. Appl. No. 11/223,718, 11 pages.
Request for Continued Examination and Amendment and Response to Final Office Action dated May 18, 2009, U.S. Appl. No. 11/223,718, 19 pages.
Supplementary Declaration filed May 18, 2009, U.S. Appl. No. 11/223,718, 27 pages.
Notice of Non-Compliant Amendment dated May 21, 2009, U.S. Appl. No. 11/223,718, 2 pages.
Response to Notice of Non-Compliant Amendment dated Jun. 22, 2009, U.S. Appl. No. 11/223,718, 16 pages.
Office Action dated Jul. 24, 2009, U.S. Appl. No. 11/223,718, 12 pages.
Amendment and Response to Office Action dated Oct. 26, 2009, U.S. Appl. No. 11/223,718, 9 pages.
Final Office Action dated Dec. 2, 2009, U.S. Appl. No. 11/223,718, 10 pages.
Examiner's Interview Summary dated Mar. 23, 2010, U.S. Appl. No. 11/223,718, 4 pages.
Examiner's Interview Summary dated May 20, 2010, U.S. Appl. No. 11/223,718, 4 pages.
Notice of Appeal and Interview Summary dated Jun. 2, 2010, U.S. Appl. No. 11/223,718, 3 page.
Request for Continued Examination and Amendment and Response to Final Office Action dated Jan. 3, 2011, U.S. Appl. No. 11/223,718, 11 pages.
Office Action dated Jan. 24, 2011, U.S. Appl. No. 11/223,718, 13 pages.
Amendment and Response to Office Action dated Jun. 24, 2011, U.S. Appl. No. 11/223,718, 14 pages.
Final Office Action dated Jul. 14, 2011, U.S. Appl. No. 11/223,718, 5 pages.
Request for Continued Examination and Amendment and Response to Final Office Action dated Sep. 22, 2011, U.S. Appl. No. 11/223,718, 7 pages.
Notice of Allowance and Fee(s) Due dated Nov. 28, 2011, U.S. Appl. No. 11/223,718, 8 pages.
Office Action (Restriction Requirement) dated Mar. 10, 2009, U.S. Appl. No. 11/860,232, 6 pages.
Amendment and Response to Restriction Requirement dated Apr. 10, 2009, U.S. Appl. No. 11/860,232, 5 pages.
Interview Summary dated Jun. 4, 2009, USSN 860,232, 3 pages.
Notice of Allowance and Fee(s) Due dated Aug. 7, 2009, U.S. Appl. No. 11/860,232, 17 pages.
Request for Continued Examination dated Nov. 6, 2009, U.S. Appl. No. 11/860,232, 1 page.
Interview Summary dated Nov. 16, 2009, U.S. Appl. No. 11/860,232, 15 pages.
Notice of Allowance and Fee(s) Due dated Dec. 2, 2009, U.S. Appl. No. 11/860,232, 4 pages.
Office Action dated Nov. 23, 2012, U.S. Appl. No. 95/002,396, 39 pages.
Office Action dated Nov. 23, 2012, U.S. Appl. No. 95/002,405, 37 pages.
Office Action dated Nov. 23, 2012, U.S. Appl. No. 95/002,411, 38 pages.
Amendment and Response to Office Action filed Jan. 23, 2013 and refiled on May 10, 2013, U.S. Appl. No. 95/002,396, 126 pages.
Amendment and Response to Office Action filed Jan. 23, 2013, U.S. Appl. No. 95/002,405, 117 pages.
Amendment and Response to Office Action filed Jan. 23, 2013, U.S. Appl. No. 95/002,411, 68 pages.
Third Party Requestor's Comments on Patent Owner's Amendment filed May 10, 2013, Inter Partes Reexamination of US. Patent No. 8,124,072, Jun. 10, 2013, 52 pages [resubmission of Comments filed Feb. 22, 2013].
Action Closing Prosecution dated Jul. 8, 2013, U.S. Appl. No. 95/002,396, 45 pages.
Action Closing Prosecution dated Jul. 3, 2013, U.S. Appl. No. 95/002,405, 38 pages.
Action Closing Prosecution dated Jul. 3, 2013, U.S. Appl. No. 95/002,411, 35 pages.
Petition for Withdrawal of Action Closing Prosecution and Requesting Prosecution be Reopened and Comments Pursuant to Action Closing Prosecution, U.S. Appl. No. 95/002,396, filed Aug. 8, 2013, 79 pages.
Petition for Withdrawal of Action Closing Prosecution and Requesting Prosecution be Reopened and Comments Pursuant to Action Closing Prosecution, U.S. Appl. No. 95/002,405, filed Aug. 5, 2013, 79 pages.
Petition for Withdrawal of Action Closing Prosecution and Requesting Prosecution be Reopened and Comments Pursuant to Action Closing Prosecution, U.S. Appl. No. 95/002,411, filed Aug. 5, 2013, 79 pages.
Notice of Allowance and Fee(s) Due dated Jun. 25, 2013, U.S. Appl. No. 13/406,794, 6 pages.
Office Action dated Jul. 11, 2013, U.S. Appl. No. 13/357,402, 10 pages.

* cited by examiner

SOLUBILIZED COQ-10

CROSS-REFERENCE TO RELATED APPLICATION(S)

This application is a continuation of U.S. patent application Ser. No. 10/674,268, filed Sep. 29, 2003, entitled "Solubilized CoQ-10," which is hereby incorporated herein by reference in its entirety.

FIELD OF THE INVENTION

The present invention relates to the solubilization of coenzyme Q-10 and analogs thereof in monoterpenes, thereby providing increased bioavailability in delivery.

BACKGROUND OF THE INVENTION

CoQ-10 (coenzyme Q10) is a fat-soluble quinone that is structurally similar to vitamin K and commonly known as ubiquinone. CoQ-10 is found in most living organisms, and is essential for the production of cellular energy. CoQ-10 (2,3 dimethyl-5 methyl-6-decaprenyl benzoquinone) is an endogenous antioxidant found in small amounts in meats and seafood. Although CoQ-10 is found in all human cells, the highest concentrations of CoQ-10 occur in the heart, liver, kidneys, and pancreas. It is found naturally in the organs of many mammalian species.

CoQ-10 can be synthesized in the body or it can be derived from dietary sources. Situations may arise, however, when the need for CoQ-10 surpasses the body's ability to synthesize it. CoQ-10 can be absorbed by oral supplementation as evidenced by significant increases in serum CoQ-10 levels after supplementation.

CoQ-10 is an important nutrient because it lies within the membrane of a cell organelle called the mitochondria. Mitochondria are known as the "power house" of the cell because of their ability to produce cellular energy, or ATP, by shuttling protons derived from nutrient breakdown through the process of aerobic (oxygen) metabolism. CoQ-10 also has a secondary role as an antioxidant. CoQ-10, due to the involvement in ATP synthesis, affects the function of almost all cells in the body, making it essential for the health of all human tissues and organs. CoQ-10 particularly effects the cells that are the most metabolically active: heart, immune system, gingiva, and gastric mucosa Several clinical trials have shown CoQ-10 to be effective in supporting blood pressure and cholesterol levels. Furthermore, CoQ-10 has also been shown to improve cardiovascular health. CoQ-10 has been implicated as being an essential component in thwarting various diseases such as certain types of cancers. These facts lead many to believe that CoQ-10 supplementation is vital to an individual's well being.

CoQ-10 is sparingly soluble in most hydrophilic solvents such as water. Therefore, CoQ-10 is often administered in a powdered form, as in a tablet or as a suspension. However, delivery of CoQ-10 by these methods limits the bioavailability of the material to the individual.

There is a need in the art for an improved methodology to deliver increased amount of bioavailable CoQ-10 to an individual in need thereof.

BRIEF SUMMARY OF THE INVENTION

The present invention pertains to the surprising discovery that ubiquinone (CoQ-10) can be readily dissolved in varying concentrations in monoterpenes. Generally, until the present discovery, most CoQ-10 liquid delivery methods could solubilize only up to about 5% by weight of the CoQ-10 in the "solvent". Typical solvents included various oils or the CoQ-10 was held in suspension. The present invention provides the ability to solubilize CoQ-10 in monoterpenes in concentrations of up to about 60% (weight to weight) without the need to aggressively heat the solution or with gentle warming. In particular, the solubilization of the CoQ-10 with monoterpenes can be accomplished at ambient temperatures.

In one aspect, the present invention pertains to compositions that include coenzyme Q-10 or an analog thereof with a sufficient quantity of a monoterpene that is suitable to solubilize said coenzyme Q-10 and a pharmaceutically acceptable carrier. Generally, about 30 to about 45% of the CoQ-10 (by weight) is solubilized in the monoterpene. In particular, the monoterpene is limonene. The compositions of the invention are useful as dietary supplements or as nutraceuticals.

In particular, the compositions of the invention are included in a soft gelatin (soft gel) capsule. Typically, the soft gelatin capsule includes at least 5% by weight of coenzyme Q-10 or an analog thereof solubilized in a monoterpene. Typical monoterpenes include, for example, perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

In another embodiment, the present invention pertains to methods for delivery of an effective amount of bioavailable CoQ-10 to an individual. The method includes providing CoQ-10 solubilized in a monoterpene, such that an effective amount of CoQ-10 is provided to the individual.

In still another embodiment, the present invention also includes packaged formulations of the invention that include a monoterpene as a solvent for the CoQ-10 and instructions for use of the tablet, capsule, elixir, etc.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The present invention pertains to the surprising discovery that ubiquinone (CoQ-10) can be readily dissolved in varying concentrations in monoterpenes. CoQ-10 is found in most living organisms, and is essential for the production of cellular energy. Ubiquinone is a naturally occurring hydrogen carrier in the respiratory chain (coenzyme Q) and structurally, it is a 2,3-dimethoxy-5-methyl-1,4-benzoquinone with a multiprenyl side chain, the number of isoprene units varying depending upon the organism from which it is derived. CoQ-10 analogs include reduced and semi-reduced CoQ-10 and ubiquinone derivatives described, for example, in WO 8803015, the teachings of which are incorporated herein by reference.

Generally, until the present discovery, most CoQ-10 liquid delivery methods could solubilize only up at most about 10% by weight of the CoQ-10 in the "solvent. Typical solvents included oils or the CoQ-10 was held in an aqueous suspension. Alternatively, the CoQ-10 was provided as a solid in a tablet or powder.

The present invention provides the ability to solubilize CoQ-10 in monoterpenes, as defined herein, in concentrations of up to about 60% (weight to weight) without the need to heat the solution. In one aspect, the monoterpene solubilizes CoQ-10 from about 0.1 percent by weight to about 45 percent by weight.

In particular, the solubilization of the CoQ-10 with monoterpenes can be accomplished at ambient temperatures. In one aspect, from about 5 to about 50 percent (weight CoQ-10/weight solvent) CoQ-10 can be solubilized in a monoterpene. In another aspect, from about 15 to about 40 percent w/w can be solubilized and in still another aspect, from about 20 to about 35 percent w/w CoQ-10 can be solubilized in a monoterpene.

The phrase "sufficient quantity of a monoterpene suitable to solubilize coenzyme Q-10" is therefore intended to mean that that amount of a monoterpene that will dissolve CoQ-10 under a given set of conditions, generally, those at ambient temperature. This determination should be understood by one skilled in the art and can be determined by methods known in the art, such as by solubility studies.

One of the particular advantages of utilizing monoterpenes in combination with CoQ-10 is that the enzyme is dissolved by the monoterpene. That is, many formulations currently in the marketplace have CoQ-10 present as a suspension; a situation where not all the CoQ-10 is dissolved. This reduces efficacy and the bioavailability of the CoQ-10. The present invention eliminates this disadvantage by solubilizing the CoQ-10 in the monoterpene.

A particular advantage in using monoterpenes is that the CoQ-10 does not have to be heated to dissolve into solution. This is important so that the CoQ-10 does not degrade upon dissolution.

The term "monoterpene" as used herein, refers to a compound having a 10-carbon skeleton with non-linear branches. A monoterpene refers to a compound with two isoprene units connected in a head-to-end manner. The term "monoterpene" is also intended to include "monoterpenoid", which refers to a monoterpene-like substance and may be used loosely herein to refer collectively to monoterpenoid derivatives as well as monoterpenoid analogs. Monoterpenoids can therefore include monoterpenes, alcohols, ketones, aldehydes, ethers, acids, hydrocarbons without an oxygen functional group, and so forth.

It is common practice to refer to certain phenolic compounds, such as eugenol, thymol and carvacrol, as monoterpenoids because their function is essentially the same as a monoterpenoid. However, these compounds are not technically "monoterpenoids" (or "monoterpenes") because they are not synthesized by the same isoprene biosynthesis pathway, but rather by production of phenols from tyrosine. However, common practice will be followed herein. Suitable examples of monoterpenes include, but are not limited to, limonene, pinene, cintronellol, terpinene, nerol, menthane, carveol, S-linalool, safrol, cinnamic acid, apiol, geraniol, thymol, citral, carvone, camphor, etc. and derivatives thereof. For information about the structure and synthesis of terpenes, including terpenes of the invention, see Kirk-Othmer Encyclopedia of Chemical Technology, Mark, et al., eds., 22:709-762 3d Ed (1983), the teachings of which are incorporated herein in their entirety.

In particular, suitable limonene derivatives include perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

Formulation of the CoQ-10 can be accomplished by many methods known in the art. For example, the solubilized CoQ-10 can be formulated in a suspension, an emulsion, an elixir, a solution, a caplet that harbors the liquid, or in a soft gelatin capsule. Often the formulation will include an acceptable carrier, such as an oil, or other suspending agent.

Suitable carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carrier, beeswax can be used as a suitable carrier, as well as suspending agents such as silica (silicon dioxide).

The formulations of the invention are considered dietary supplements useful to the increase the amounts of CoQ-10 in the individuals in need thereof.

Alternatively, the formulations of the invention are also considered to be nutraceuticals. The term "nutraceutical" is recognized in the art and is intended to describe specific chemical compounds found in foods that may prevent disease. CoQ-10 is one such compound.

The formulations of the invention can further include various ingredients to help stabilize, or help promote the bioavailability of the CoQ-10, or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals may be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Vitamin(s), if present, are present in the composition of the invention in an amount ranging from about 5 mg to about 500 mg. More particularly, the vitamin(s) is present in an amount ranging from about 10 mg to about 400 mg. Even more specifically, the vitamin(s) is present from about 250 mg to about 400 mg. Most specifically, the vitamin(s) is present in an amount ranging from about 10 mg to about 50 mg. For example, B vitamins are in usually incorporated in the range of about 1 milligram to about 10 milligrams, i.e., from about 3 micrograms to about 50 micrograms of B 12. Folic acid, for example, is generally incorporated in a range of about 50 to about 400 micrograms, biotin is generally incorporated in a range of about 25 to about 700 micrograms and cyanocobalamin is incorporated in a range of about 3 micrograms to about 50 micrograms.

Mineral(s), if present, are present in the composition of the invention in an amount ranging from about 25 mg to about 1000 mg. More particularly, the mineral(s) are present in the composition ranging from about 25 mg to about 500 mg. Even more particularly, the mineral(s) are present in the composition in an amount ranging from about 100 mg to about 600 mg.

Various additives can be incorporated into the present compositions. Optional additives of the present composition include, without limitation, phospholipids, L-carnitine, starches, sugars, fats, antioxidants, amino acids, proteins, flavorings, coloring agents, hydrolyzed starch(es) and derivatives thereof or combinations thereof.

As used herein, the term "phospholipid" is recognized in the art, and refers to phosphatidyl glycerol, phosphatidyl inositol, phosphatidyl serine, phosphatidyl choline, phosphatidyl ethanolamine, as well as phosphatidic acids, ceramides, cerebrosides, sphingomyelins and cardiolipins.

L-carnitine is recognized in the art and facilitates transport of materials through the mitochondrial membrane. L-carnitine is an essential fatty acid metabolism cofactor that helps to move fatty acids to the mitochondria from the cytoplasm. This is an important factor as this is where CoQ-10 uptake occurs.

In one aspect of the present invention, L-carnitine is included in soft gel formulations in combination with CoQ-10. Suitable ratios of L-carnitine and CoQ-10 are known in the art and include those described in U.S. Pat. No. 4,599,232, issued to Sigma Tau Industrie Faramaceutiche Riunite S.p.A. on Jul. 8, 1986, the teachings of which are incorporated herein in their entirety. In particular, combinations of limonene, CoQ-10 and L-carnitine in soft gel formulations are of importance. The present invention provides the advantage of solvating large amounts (relative to that of current state of the art) of CoQ-10 in limonene in a soft gel capsule along with an additive, such as L-carnitine.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and E and beta-carotene; natural components such as camosol, carnosic acid and rosmanol found in rosemary and hawthorn extract, proanthocyanidins such as those found in grapeseed or pine bark extract, and green tea extract.

The term "flavonoid" as used herein is recognized in the art and is intended to include those plant pigments found in many foods that are thought to help protect the body from cancer. These include, for example, epi-gallo catechin gallate (EGCG), epi-gallo catechin (EGC) and epi-catechin (EC).

Any dosage form, and combinations thereof, are contemplated by the present invention. Examples of such dosage forms include, without limitation, chewable tablets, elixirs, liquids, solutions, suspensions, emulsions, capsules, soft gelatin capsules, hard gelatin capsules, caplets, lozenges, chewable lozenges, suppositories, creams, topicals, ingestibles, injectables, infusions, health bars, confections, animal feeds, cereals, cereal coatings, and combinations thereof. The preparation of the above dosage forms are well known to persons of ordinary skill in the art.

For example, health bars can be prepared, without limitation, by mixing the formulation plus excipients (e.g., binders, fillers, flavors, colors, etc.) to a plastic mass consistency. The mass is then either extended or molded to form "candy bar" shapes that are then dried or allowed to solidify to form the final product.

Soft gel or soft gelatin capsules can be prepared, for example, without limitation, by dispersing the formulation in an appropriate vehicle (e.g. rice bran oil, monoterpene and/or beeswax) to form a high viscosity mixture. This mixture is then encapsulated with a gelatin based film using technology and machinery known to those in the soft gel industry. The industrial units so formed are then dried to constant weight. Typically, the weight of the capsule is between about 100 to about 2500 milligrams and in particular weigh between about 1500 and about 1900 milligrams, and more specifically can weigh between about 1500 and about 2000 milligrams.

For example, when preparing soft gelatin shells, the shell can include between about 20 to 70 percent gelatin, generally a plasticizer and about 5 to about 60% by weight sorbitol. The filling of the soft gelatin capsule is liquid (principally limonene, in combination with rice bran oil and/or beeswax if desired) and can include, apart form the antioxidant actives, a hydrophilic matrix. The hydrophilic matrix, if present, is a polyethylene glycol having an average molecular weight of from about 200 to 1000. Further ingredients are optionally thickening agents. In one embodiment, the hydrophilic matrix includes polyethylene glycol having an average molecular weight of from about 200 to 1000, 5 to 15% glycerol, and 5 to 15% by weight of water. The polyethylene glycol can also be mixed with propylene glycol and/or propylene carbonate.

In another embodiment, the soft gel capsule is prepared from gelatin, glycerine, water and various additives. Typically, the percentage (by weight) of the gelatin is between about 30 and about 50 weight percent, in particular between about 35 and about weight percent and more specifically about 42 weight percent. The formulation includes between about 15 and about 25 weight percent glycerine, more particularly between about 17 and about 23 weight percent and more specifically about 20 weight percent glycerine.

The remaining portion of the capsule is typically water. The amount varies from between about 25 weigh percent and about 40 weight percent, more particularly between about 30 and about 35 weight percent, and more specifically about 35 weight percent. The remainder of the capsule can vary, generally, between about 2 and about 10 weight percent composed of a flavoring agent(s), sugar, coloring agent(s), etc. or combination thereof. After the capsule is processed, the water content of the final capsule is often between about 5 and about 10 weight percent, more particularly 7 and about 12 weight percent, and more specifically between about 9 and about 10 weight percent.

As for the manufacturing, it is contemplated that standard soft shell gelatin capsule manufacturing techniques can be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes are mature technologies and are all widely available to any one wishing to prepare soft gelatin capsules.

Typically, when a soft gel capsule is prepared, the total weight is between about 250 milligrams and about 2.5 gram in weight, e.g., 400-750 milligrams. Therefore, the total weight of additives, such as vitamins and antioxidants, is between about 80 milligrams and about 2000 milligrams, alternatively, between about 100 milligrams and about 1500 milligrams, and in particular between about 120 milligrams and about 1200 milligrams.

For example, a soft gel capsule can be prepared by mixing a 35% solution of CoQ-10 and limonene (w/w) (e.g., 104 milligrams of CoQ-10 in 193.14 milligrams of limonene) with between about 0.01 grams and about 0.4 grams (e.g., 0.1 grams) tocopherol, between about 200 grams and about 250 grams (e.g., 225 grams) rice bran oil and between about 0.01 grams and about 0.5 grams betacarotene (e.g. about 0.02 grams). The mixture is then combined with encapsulated within a gelatin capsule as described above.

The present invention also provides packaged formulations of a monoterpene with CoQ-10 and instructions for use of the tablet, capsule, elixir, etc. Typically, the packaged formulation, in whatever form, is administered to an individual in need thereof that requires and increase in the amount of CoQ-10 in the individual's diet. Typically, the dosage requirements is between about 1 to about 4 dosages a day.

CoQ-10 has been implicated in various biochemical pathways and is suitable for the treatment of cardiovascular conditions, such as those associated with, for example, statin drugs that effect the body's ability to product coQ-10 naturally. CoQ-10 has also been implicated in various periodontal diseases. Furthermore, CoQ-10 has been implicated in mitochondrial related diseases and disorders, such as the inability to product acetyl coenzyme A, neurological disorders, for example, such as Parkinson's disease and, Prater-Willey syndrome.

The following examples are intended to be illustrative only and should not be considered limiting.

Examples

Formulations of CoQ-10 can be prepared in the following ratios by mixing the components together and then placing into a soft gel capsule.

| Component | Example 1 | Example 2 |
|---|---|---|
| CoQ-10 | 104.09 mg | 104.09 mg |
| Mixed Tocopherols (372 IU/g) | 269.03 mg | 269.03 mg |
| Rice Bran Oil | 176.02 mg | — |
| Natural Beta Carotene (20% by weight) | 10.05 mg | 10.05 mg |
| Yellow Beeswax | 20.0 mg | — |
| D-limonene | — | 196.02 mg |
| Total weight | 580 mg | 580 mg |

Example 2 demonstrates that the use of limonene solubilizes CoQ-10 without the requirement of beeswax and/or rice bran oil being present. Examples 1 and 2 could be incorporated into soft gel capsules by standard methods known in the art.

| Component | Example 3 | Example 4 |
|---|---|---|
| CoQ-10 | 17.95 g | 17.95 g |
| EPAX 2050TG | 48.77 g | 45.49 g |
| D-Limonene | 35.70 g | 35.70 g |
| 5-67 Tocopherol (1000 IU/g) | — | 0.86 g |

Examples 3 and 4 demonstrate that CoQ-10 can be solubilized in scalable quantities. Additives, such as EPAX 2050 TG (an ω-3 oil; 20% EPA/50% DHA as triglycerides, remainder fatty acid/triglycerides; Pronova Biocare) and tocopherols (5-67 Tocopherol; BD Industries) can easily be incorporated into such limonene containing formulations. The resultant mixtures contained approximately 100 mg of CoQ-10 per soft gel capsule. Preparation of the soft gel capsules was accomplished by methods well known in the art.

Although the present invention has been described with reference to preferred embodiments, persons skilled in the art will recognize that changes may be made in form and detail without departing from the spirit and scope of the invention.

All literature and patent references cited throughout the application are incorporated by reference into the application for all purposes.

What is claimed is:

1. A soft gelatin capsule, comprising
    coenzyme Q-10 solubilized in limonene to form a solution, with the proviso that the coenzyme Q-10 solubilized in the limonene is not in an emulsion, or suspension.

2. The soft gelatin capsule of claim 1, wherein said coenzyme Q-10 is selected from the group consisting of oxidized coenzyme Q-10, reduced coenzyme Q-10, and semi-reduced coenzyme Q-10.

3. The soft gelatin capsule of claim 1, wherein said soft gelatin capsule further comprises an antioxidant.

4. The soft gelatin capsule of claim 1, wherein said soft gelatin capsule further comprises a tocopherol.

5. The soft gelatin capsule of claim 1, further comprising a carrier.

6. The soft gelatin capsule of claim 5, wherein said carrier is an oil.

7. The soft gelatin capsule of claim 6, wherein said oil is rice bran oil.

8. The soft gelatin capsule of claim 2, wherein the amount of coenzyme Q-10 in said solution is about 0.1 percent up to about 60 percent coenzyme Q-10 by weight.

9. The soft gelatin capsule of claim 2, wherein the amount of coenzyme Q-10 in said solution is about 0.1 percent up to about 50 percent coenzyme Q-10 by weight.

10. The soft gelatin capsule of claim 2, wherein the amount of coenzyme Q-10 in said solution is about 0.1 percent up to about 45 percent coenzyme Q-10 by weight.

11. The soft gelatin capsule of claim 2, wherein the amount of coenzyme Q-10 in said solution is about 0.1 percent up to about 40 percent coenzyme Q-10 by weight.

12. The soft gelatin capsule of claim 2, wherein the amount of coenzyme Q-10 in said solution is about 0.1 percent up to about 35 percent coenzyme Q-10 by weight.

13. The soft gelatin capsule of claim 2, wherein the amount of coenzyme Q-10 in said solution is about 15 percent up to about 60 percent coenzyme Q-10 by weight.

14. The soft gelatin capsule of claim 2, wherein the amount of coenzyme Q-10 in said solution is about 15 percent up to about 50 percent coenzyme Q-10 by weight.

15. The soft gelatin capsule of claim 2, wherein the amount of coenzyme Q-10 in said solution is about 15 percent up to about 45 percent coenzyme Q-10 by weight.

16. The soft gelatin capsule of claim 2, wherein the amount of coenzyme Q-10 in said solution is about 15 percent up to about 40 percent coenzyme Q-10 by weight.

17. The soft gelatin capsule of claim 2, wherein the amount of coenzyme Q-10 in said solution is about 15 percent up to about 35 percent coenzyme Q-10 by weight.

18. The soft gelatin capsule of claim 2, wherein the amount of coenzyme Q-10 in said solution is about 20 percent up to about 60 percent coenzyme Q-10 by weight.

19. The soft gelatin capsule of claim 2, wherein the amount of coenzyme Q-10 in said solution is about 20 percent up to about 50 percent coenzyme Q-10 by weight.

20. The soft gelatin capsule of claim 2, wherein the amount of coenzyme Q-10 in said solution is about 20 percent up to about 45 percent coenzyme Q-10 by weight.

21. The soft gelatin capsule of claim 2, wherein the amount of coenzyme Q-10 in said solution is about 20 percent up to about 40 percent coenzyme Q-10 by weight.

22. The soft gelatin capsule of claim 2, wherein the amount of coenzyme Q-10 in said solution is about 20 percent up to about 35 percent coenzyme Q-10 by weight.

23. The soft gelatin capsule of claim 2, wherein the amount of coenzyme Q-10 in said solution is about 30 percent up to about 60 percent coenzyme Q-10 by weight.

24. The soft gelatin capsule of claim 2, wherein the amount of coenzyme Q-10 in said solution is about 30 percent up to about 50 percent coenzyme Q-10 by weight.

25. The soft gelatin capsule of claim 2, wherein the amount of coenzyme Q-10 in said solution is about 30 percent up to about 45 percent coenzyme Q-10 by weight.

26. The soft gelatin capsule of claim 2, wherein the amount of coenzyme Q-10 in said solution is about 30 percent up to about 40 percent coenzyme Q-10 by weight.

27. The soft gelatin capsule of claim 2, wherein the amount of coenzyme Q-10 in said solution is about 30 percent up to about 35 percent coenzyme Q-10 by weight.

28. The soft gelatin capsule of claim 2, wherein said coenzyme Q-10 is oxidized coenzyme Q-10.

29. The soft gelatin capsule of claim 1, wherein said coenzyme Q-10 is reduced coenzyme Q-10.

30. The soft gelatin capsule of claim 1, wherein said coenzyme Q-10 is semi-reduced coenzyme Q-10.

31. A packaged nutraceutical formulation comprising:
(a) coenzyme Q-10 and a sufficient quantity of limonene suitable to solubilize said coenzyme Q-10 to form a solution,
with the proviso that the coenzyme Q-10 solubilized in the limonene is not in an emulsion, or suspension, and wherein said formulation is encapsulated in a gelatin capsule; and
(b) instructions for the use thereof.

32. The packaged nutraceutical formulation of claim 31, wherein said coenzyme Q-10 is selected from the group consisting of oxidized coenzyme Q-10, reduced coenzyme Q-10, and semi-reduced coenzyme Q-10.

33. The packaged nutraceutical of claim 31, wherein said soft gelatin capsule further comprises an antioxidant.

34. The packaged nutraceutical of claim 31, wherein said soft gelatin capsule further comprises a tocopherol.

35. The packaged nutraceutical of claim 31, further comprising a carrier.

36. The packaged nutraceutical of claim 32, wherein said carrier is an oil.

37. The packaged nutraceutical of claim 33, wherein said oil is rice bran oil.

38. The packaged nutraceutical formulation of claim 29, wherein said coenzyme Q-10 is oxidized coenzyme Q-10.

39. The packaged nutraceutical formulation of claim 29, wherein said coenzyme Q-10 is reduced coenzyme Q-10.

40. The packaged nutraceutical formulation of claim 29, wherein said coenzyme Q-10 is semi-reduced coenzyme Q-10.

* * * * *